United States Patent
Shuber (10) Patent No.: US 6,818,404 B2
(45) Date of Patent: Nov. 16, 2004

(54) METHODS FOR DETECTING HYPERMETHYLATED NUCLEIC ACID IN HETEROGENEOUS BIOLOGICAL SAMPLES

(75) Inventor: Anthony P. Shuber, Mendon, MA (US)

(73) Assignee: Exact Sciences Corporation, Marlborough, MA (US)

( * ) Notice: Subject to any disclaimer, the term of this patent is extended or adjusted under 35 U.S.C. 154(b) by 0 days.

(21) Appl. No.: 10/123,071

(22) Filed: Apr. 11, 2002

(65) Prior Publication Data

US 2003/0087258 A1 May 8, 2003

Related U.S. Application Data (63) Continuation-in-part of application No. 09/870,729, filed on May 30, 2001, which is a continuation of application No. 09/177,243, filed on Oct. 22, 1998, now abandoned.
(60) Provisional application No. 60/063,219, filed on Oct. 23, 1997.

(51) Int. Cl.⁷ .......................... C12Q 1/68; C12P 19/34; C07H 21/04; G01N 33/48
(52) U.S. Cl. ..................... 435/6; 435/91.1; 435/91.2; 536/24.3; 436/63; 436/64
(58) Field of Search .................... 435/6, 91.1, 91.2; 436/63, 64; 536/24.3

(56) References Cited

U.S. PATENT DOCUMENTS

| | | |
|---|---|---|
| 4,965,188 A | 10/1990 | Mullis et al. |
| 5,633,134 A | 5/1997 | Shuber |
| 5,670,325 A | 9/1997 | Lapidus et al. |
| 5,741,650 A | 4/1998 | Lapidus et al. |
| 5,786,146 A | 7/1998 | Herman et al. |
| 5,830,665 A | 11/1998 | Shuber et al. |
| 5,882,856 A | 3/1999 | Shuber |
| 5,888,778 A | 3/1999 | Shuber |
| 5,928,870 A | 7/1999 | Lapidus et al. |
| 5,952,178 A | 9/1999 | Lapidus et al. |
| 6,020,137 A | 2/2000 | Lapidus et al. |
| 6,100,029 A | 8/2000 | Lapidus et al. |
| 6,143,529 A | 11/2000 | Lapidus et al. |
| 6,146,828 A | 11/2000 | Lapidus et al. |
| 6,203,993 B1 | 3/2001 | Shuber et al. |
| 6,214,558 B1 | 4/2001 | Shuber et al. |
| 6,268,136 B1 | 7/2001 | Shuber et al. |
| 6,280,947 B1 | 8/2001 | Shuber et al. |
| 6,300,077 B1 | 10/2001 | Shuber et al. |
| 6,303,304 B1 | 10/2001 | Shuber et al. |
| 6,351,857 B2 | 3/2002 | Slaon, III et al. |
| 6,406,857 B1 | 6/2002 | Shuber et al. |
| 6,415,455 B1 | 7/2002 | Slaon, III et al. |
| 6,428,964 B1 | 8/2002 | Shuber |
| 6,475,738 B2 | 11/2002 | Shuber et al. |
| 6,482,595 B2 | 11/2002 | Shuber et al. |
| 6,498,012 B2 | 12/2002 | Laken |
| 6,503,718 B2 | 1/2003 | Shuber et al. |
| 6,551,777 B1 | 4/2003 | Shuber et al. |
| 2002/0025525 A1 | 2/2002 | Shuber |
| 2002/0045183 A1 | 4/2002 | Shuber et al. |
| 2002/0110810 A1 | 8/2002 | Shuber |
| 2002/0119472 A1 | 8/2002 | Lapidus et al. |
| 2002/0132251 A1 | 9/2002 | Shuber |
| 2002/0164631 A1 | 11/2002 | Shuber et al. |
| 2003/0049659 A1 | 3/2003 | Lapidus et al. |

FOREIGN PATENT DOCUMENTS

| | | |
|---|---|---|
| EP | 0 415 755 A2 | 3/1991 |
| WO | WO 90/09455 | 8/1990 |
| WO | WO 91/15601 | 10/1991 |
| WO | WO 91/17270 | 11/1991 |
| WO | WO 92/13103 | 8/1992 |
| WO | WO 97/28450 | 8/1997 |
| WO | WO 98/39478 | 9/1998 |
| WO | WO 98/58084 | 12/1998 |
| WO | WO 99/20798 | 4/1999 |
| WO | WO 99/28507 | 6/1999 |
| WO | WO 99/53316 | 10/1999 |
| WO | WO 00/31303 | 6/2000 |
| WO | WO 00/32820 | 6/2000 |
| WO | WO 00/50640 | 8/2000 |
| WO | WO 00/58514 | 10/2000 |
| WO | WO 00/61808 | 10/2000 |
| WO | WO 00/66005 | 11/2000 |
| WO | WO 00/70096 | 11/2000 |
| WO | WO 01/11083 | 2/2001 |
| WO | WO 01/18252 | 3/2001 |
| WO | WO 01/42503 | 6/2001 |
| WO | WO 01/42781 | 6/2001 |
| WO | WO 01/64950 | 9/2001 |

(List continued on next page.)

OTHER PUBLICATIONS

Ahlquist et al., (2000), "Colorectal Cancer Screening by Detection of Altered Human DNA in Stool: Feasibility of a Multitarget Assay Panel," *Gastroenterology*, vol. 119, No. 5, pp. 1219–1227.

Dong et al., (Jun. 6, 2001), "Detecting Colorectal Cancer in Stool with the Use of Multiple Genetic Targets," *Journal of the National Cancer Institute*, vol. 93, No. 11, pp. 858–865.

Esteller et al., (Aug. 15, 2000), "Analysis of *Adenomatous Polyposis Coli* Promoter Hypermethylation in Human Cancer," *Cancer Research*, vol. 60, pp. 4366–4371.

(List continued on next page.)

*Primary Examiner*—Kenneth R. Horlick
*Assistant Examiner*—Joyce Tung
(74) *Attorney, Agent, or Firm*—Mintz, Levin, Cohn, Ferris, Glovsky and Popeo, P.C.; Ivor R. Elrifi, Esq.; Naomi S. Biswas, Esq.

(57) ABSTRACT

The invention provides amplification-based methods for detecting hypermethylated nucleic acid in heterogeneous biological samples, e.g., stool. A screening procedure based on the detection of hypermethylation, preferably at multiple genes, provides a means for detecting various diseases, e.g., colorectal cancer. By using chimeric primers that contain a 5' non-specific portion, the specificity and efficiency of the nucleic acid amplification is improved. Methods of the invention are especially useful in detection of rare events in a heterogeneous sample.

11 Claims, 2 Drawing Sheets

FOREIGN PATENT DOCUMENTS

| | | |
|---|---|---|
| WO | WO 01/77375 A2 | 10/2001 |
| WO | WO 01/92565 A2 | 12/2001 |
| WO | WO 02/00927 A2 | 1/2002 |
| WO | WO 02/055740 | 7/2002 |
| WO | WO 02/059379 | 8/2002 |
| WO | WO 02/074995 | 9/2002 |
| WO | WO 02/092858 | 11/2002 |
| WO | WO 03/044217 | 5/2003 |

OTHER PUBLICATIONS

Herman et al., (Sep. 1996), Methylation–specific PCR: A novel PCR assay for methylation status of CpG islands, *Proc. Natl. Acad. Sci*, vol. 93, pp. 9821–9826.

Shuber et al., (1995), "A Simplified Procedure for Developing Multiplex PCRs," *Genome Research*, vol. 5, pp. 488–493 (USA).

Shuber et al., (Jan. 2002), "Accurate, Noninvasive Detection of *Helicobacter pylori* DNA from Stool Sample: Potential Usefulness for Monitoring Treatment," *Journal of Clinical Microbiology*, vol. 40, No. 1, pp. 262–264.

Traverso et al., (Jan. 31, 2002), "Detection of *APC* Mutations in Fecal DNA from Patients with Colorectal Tumors," *New England Journal of Medicine*, vol. 346, No. 5, pp. 311–320.

Weighardt et al., (1993), "A Simple Procedure for Enhancing PCR Specificity," *PCR Methods and Application*, by Cold Spring Harbor Laboratory Press, vol. 3, pp. 77–80.

Ahlquist et al., (May, 2000), "Universal Detection of Aerodigestive Cancers by Assay of Nonapoptotic Human DNA in Stool," Presentation at Digestive Disease Week Annual Conference.

Anker et al., (2002), "Progress in the Knowledge of Circulating Nucleic Acids: Plasma RNA is Particle–Associated. Can it Become a General Detection Marker for a Cancer Blood Test?" *Clinical Chemistry*, vol. 48, No. 8, pp. 1210–1211.

Böhn et al., (1997), "Deletion Analysis at the Del–27, APC and MTS1 Loci in Bladder Cancer: LOH at the Del–27 Locus on 5p13–12 is a Prognostic Marker of Tumor Progression," *Int. J. Cancer*, vol. 74 pp. 291–295.

Kawakami et al., (Nov. 15, 2000), "Hypermethylated APC DNA in Plasma and Prognosis of Patients with Esophageal Adenocarcinoma," *Journal of the National Cancer Institute*, vol 92, No. 22, pp. 1805–1811.

Ko et al., (1999), "Genomic Instability and Alterations in *Apc, Mcc* and *Dcc* in Hong Kong Patients with Colorectal Carcinoma," *Int. J. Cancer*, vol. 84, pp. 404–409.

Shuber et al., (May 22, 2001), "Accurate Non–invasive Detection of *H. pylori* DNA Before and After Treatment," Summary to Oral Presentation.

Traverso et al., (Feb. 2, 2002), "Detection of Proximal Colorectal Cancers through Analysis of Faecal DNA," *The Lancet*, vol. 359, pp. 403–404.

METHODS FOR DETECTING HYPERMETHYLATED NUCLEIC ACID IN HETEROGENEOUS BIOLOGICAL SAMPLES

RELATED APPLICATIONS

This application is a continuation-in-part of co-owned U.S. patent application Ser. No. 09/870,729, filed May 30, 2001, which is a continuation of U.S. patent application Ser. No. 09/177,243, filed Oct. 22, 1998, now abandoned which, in turn, claims the benefit of the filing date of provisional application Ser. No. 60/063,219, filed Oct. 23, 1997. All the priority applications are incorporated herein by reference.

FIELD OF THE INVENTION

The invention relates generally to methods for detecting indicia of cancer in biological samples. In particular, the invention relates to methods for detecting the presence of hypermethylated nucleic acids in heterogeneous biological samples.

BACKGROUND OF THE INVENTION

In higher order eukaryotes, DNA may be methylated at cytosines located 5' to guanosine in CpG dinucleotides. This modification has important regulatory effects on gene expression, especially when involving CpG rich areas, known as CpG islands, often found in the promoter regions of many genes. Aberrant methylation of normally unmethylated CpG islands has been associated with transcriptional inactivation of defined tumor suppressor genes in human cancers, e.g., colorectal cancer. Therefore, detection of hypermethylated nucleic acid can indicate the onset of various forms of cancers.

Various methods have been described for detecting hypermethylation at specific loci on genomic DNA. One of these methods involves modification of DNA by sodium bisulfite or a comparable agent which converts all unmethylated cytosines to uracils without converting methylated cytosines, and subsequent amplification with primers specific for methylated versus unmethylated DNA. However, this and other hypermethylation detection methods require homogeneous nucleic acid samples that have a sufficient amount of the target nucleic acid. For many types of cancers, invasive procedures such as surgery are needed to obtain such a homogenous sample.

However, many biological samples, such as stool samples, are heterogeneous and may contain a small amount of mutant nucleic acid mixed with a large amount of wild-type nucleic acid. Therefore, there is a need in the art for methods to detect hypermethylation in heterogeneous biological samples.

SUMMARY OF THE INVENTION

Methods of the invention make it possible to detect a disease in biological samples without using an invasive procedure. According to the invention, by conducting a hypermethylation detection assay on a heterogeneous nucleic acid sample, such as a sample obtained from stool, small amounts of hypermethylated nucleic acids can be detected that are indicative of the presence of a disease, e.g., cancer or precancer, in a patient. In one aspect, methods of the invention involve detecting small amounts of hypermethylated nucleic acid by improving the efficiency and specificity of nucleic acid amplification. In another aspect, methods of the invention also use a combination of target CpG markers or loci to improve the reliability of detecting disease-associated hypermethylation.

In one aspect, methods of the invention comprise the utilization of improved primers for detecting hypermethylation in a target nucleic acid. In a preferred embodiment, methods of the invention comprise conducting a nucleic acid amplification using one or more (preferably two) chimeric primers. A chimeric primer, for purposes of the invention, is a primer having a 3' portion with substantial sequence specificity with the target template to be amplified (a template-specific portion) and a 5' portion that is referred to herein as a "non-specific portion" that does not hybridize with the target template. The 5' non-specific sequence preferably includes at least 5, but fewer than or equal to 30 nucleotides. Also, the 5' non-specific portion preferably has a G-C content of at least 50%. In a particularly preferred embodiment, the 5' non-specific portion of both the forward and the reverse primers are the same. The target nucleic acid may be DNA, RNA or a nucleic acid analog. Also in a preferred embodiment, the target nucleic acid is isolated from a stool sample.

In another aspect, methods of the invention comprise the optimization of reaction conditions for PCR to detect hypermethylation in a subpopulation of nucleic acids in a biological sample. In a preferred embodiment, methods of the invention comprise determining a first melting temperature for a primer in a PCR that amplifies a target nucleic acid, and conducting a PCR at a second melting temperature that is higher than the first melting temperature, using at least one chimeric primer. The melting temperature, sometimes called the annealing temperature, as referred to herein, means the temperature at which the strands of a nucleic acid hybrid are about 50% dissociated. The second melting temperature is preferably more than about 3° C. higher than the first melting temperature. In a highly preferred embodiment, the second melting temperature is about 65° C.

In another aspect, the invention provides methods for screening a population to detect patients with indicia of cancer. In preferred embodiments, a plurality of target CpG containing regions are interrogated for the presence of hypermethylation. Preferably, one or more of the following regions are assayed in patient nucleic acid isolated from a heterogeneous biological sample such as stool: HIC1, p14, HLTF, MINT2, and MINT31 regulatory regions. The presence of hypermethylation in at least one of these regions is indicative of the presence of indicia of cancer in the patient. According to the invention, hypermethylation is an amount of methylation that is greater than that found in normal tissue or normal cells isolated from a healthy patient. Accordingly, preferred methods of the invention include a negative control assay using nucleic acid from normal cells. In more preferred embodiments, methods of the invention also include a positive control assay using hypermethylated nucleic acid.

In a further aspect, methods of the invention are also useful to detect hypermethylation in a substantially homogeneous sample such as a biopsy sample.

These and other advantages and aspects of the invention will be understood upon consideration of the following detailed description thereof.

DETAILED DESCRIPTION OF THE INVENTION

The invention provides methods for detecting hypermethylated nucleic acid in a heterogeneous biological sample.

Methods of the invention involve amplifying a subpopulation of hypermethylated nucleic acid, preferably DNA, using PCR primers with high specificity. According to the invention, the target nucleic acid can be any nucleic acid of interest: human DNA, viral DNA, etc. The target nucleic acid can be a double-stranded DNA, single-stranded DNA, RNA, or a nucleic acid analog.

In heterogeneous nucleic acid samples (e.g., stool), hypermethylated target nucleic acid may be present in a small amount relative to unmethylated target nucleic acid. This represents a significant obstacle to detecting the hypermethylated nucleic acid against the background of unmethylated nucleic acid, using typical nucleic acid amplification methods. According to the invention, small relative amounts of hypermethylated nucleic acid can be detected using higher amplification efficiency. For PCR using conventional primers, for example, amplification efficiency remains around 50%–60% for each thermal cycle, even under optimal conditions. Meanwhile, as the degree of sample heterogeneity increases, tolerance for background (e.g. signal generated by the presence of normal DNA) becomes increasingly lower. According to the invention, it is necessary to retain a sufficient signal to noise ratio to distinguish positive clinical samples from negative or control samples within an assay, and for retaining high confidence in the assay results. Therefore, methods of the invention require a heightened specificity in amplification-based detection assays in order to detect a small amount of hypermethylated target nucleic acid against a background of unmethylated nucleic acid in heterogeneous biological samples.

Figure 1:
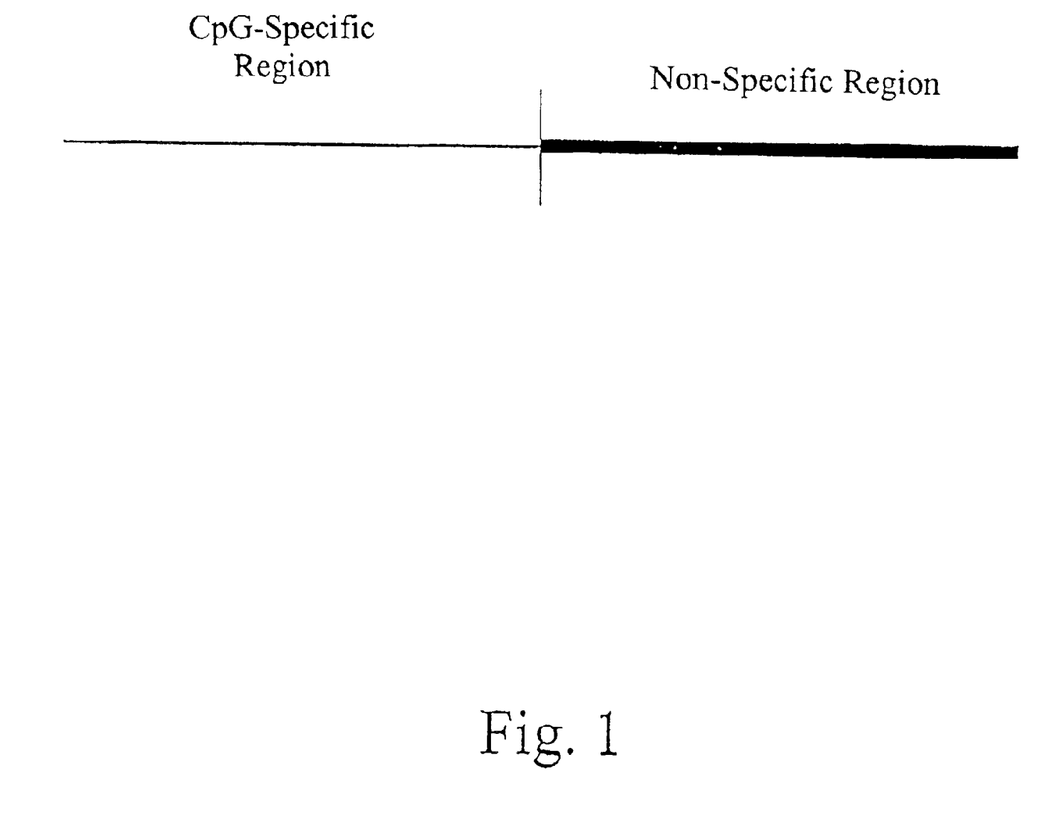
FIG. 1 shows a schematic diagram of the chimeric primers used in the present invention.

Referring to FIG. 1, according to the invention, a chimeric primer is provided that has a first portion that is not homologous or complementary to the target template ("non-specific portion" or "non-specific region"). The chimeric primer also contains a second, template-specific portion that is 3' to the first portion.

The non-specific portion maybe of any sequence, regardless of length, that does not have substantial sequence specificity (i.e., does not hybridize under stringent hybridization conditions) for any template sequence in an analyte sample. In a preferred embodiment, the non-specific portion is the 5' end of the chimeric primer. But there may be additional sequence 5' to the non-specific portion. To further prevent background binding, in a particular embodiment, the non-specific portion of the chimeric primer includes a high G-C content of at least 50%.

The template-specific portion is preferably complementary to a CpG-containing sequence on the target nucleic acid. In preferred embodiments of the invention, the CpG-containing sequence is part of a promoter or regulatory region of a gene associated with cancer, such as a tumor suppressor gene. A preferred promoter region contains a plurality of CpG dinucleotides (CpG island(s)) that are hypermethylated in cancerous cells. In more preferred embodiments of the invention, an amplification reaction is performed using a forward and a reverse chimeric primer, each of which includes a portion that is complementary to a different CpG containing sequence within the target nucleic acid region. However, in some embodiments, hypermethylation can be detected in an amplification reaction that uses only one chimeric primer that includes a portion complementary to a CpG containing sequence. In this embodiment, amplification may be conducted using a second primer that includes a portion complementary to a non CpG containing sequence adjacent the target promoter or regulatory region. According to the invention, amplification may also be performed using one chimeric primer and one non-chimeric primer, provided that the chimeric primer includes a sequence that is complementary to a CpG containing sequence on the target nucleic acid.

When a chimeric primer as described above is used in a PCR, non-specific binding to the template is reduced because matching between the template-specific portion tail and a target nucleic acid has to be more exact to offset the apparent non-matching by the non-specific portion. In other words, under the same condition, a template-specific sequence has a lower tolerance for mismatches when it is part of a chimeric primer than by itself. The specificity is even higher when the melting temperature is elevated in a preferred embodiment of the invention.

Figure 2:
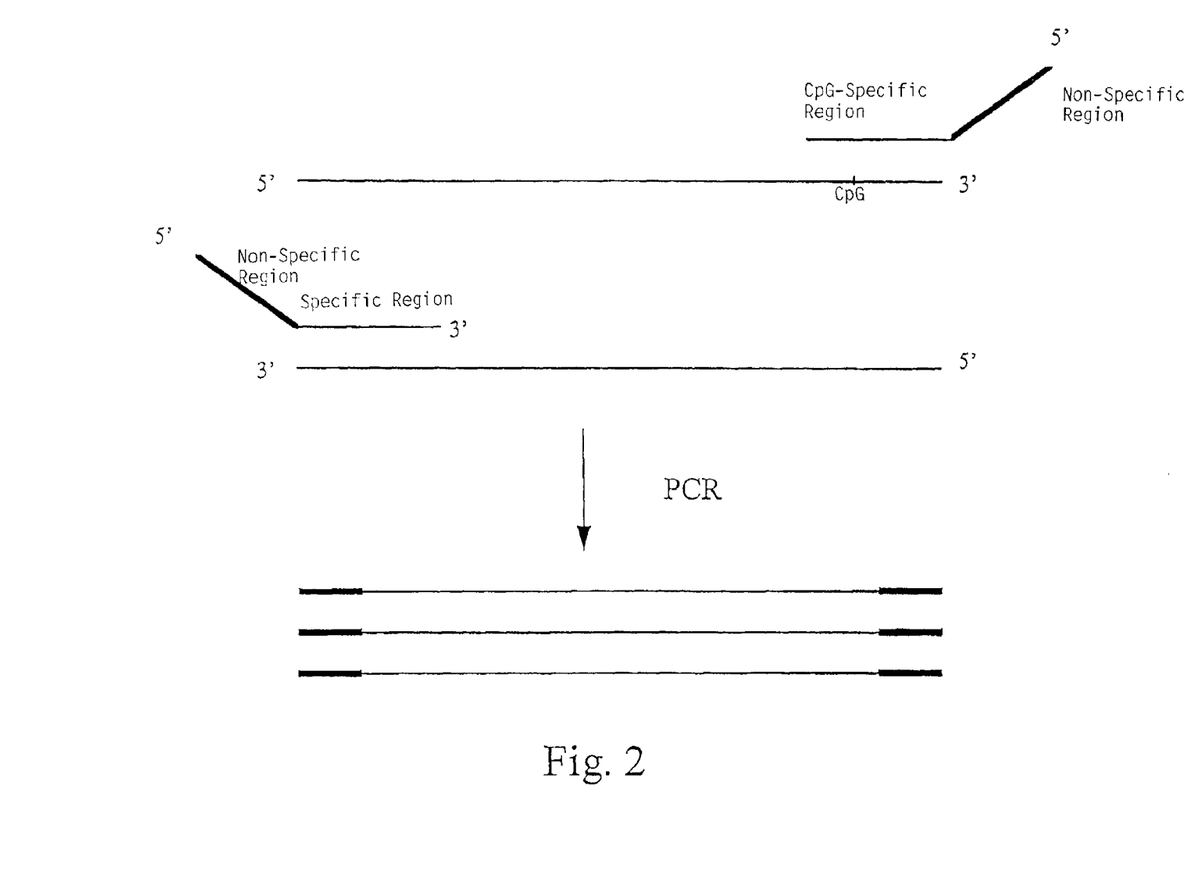
FIG. 2 shows a schematic representation of PCR amplification using chimeric primers.

Conventional PCR efficiency typically does not exceed 60% for each thermal extension cycle. When a chimeric primer according to the present invention is used, the efficiency for the first round of extension in PCR may be further compromised (e.g., 20%). However, in subsequent PCR cycles where the chimeric primer is used, extension efficiency may reach as high as 100%. This makes methods of the present invention more efficient in amplifying a specific target template over multiple PCR cycles (e.g. 20 cycles). As a result, the number of PCR cycles needed to amplify a rare event target in a heterogeneous sample for detection or further analysis can be reduced by using a chimeric primer of the invention. While reasons for the enhanced extension efficiency in the later PCR cycles while using a chimeric primer are not fully understood, it has been postulated that the enhanced efficiency might be related to the fact that, following the first round of PCR involving a chimeric primer, the non-specific sequence becomes incorporated into the PCR products (amplicon) generated from the first round PCR, (See FIG. 2), and becomes part of potential templates for binding. Overall improvement in PCR efficiency is also observed when melting temperature is elevated.

Accordingly, methods of the invention provide heightened specificity and efficiency in an amplification-based screening method that looks for hypermethylated nucleic acid in a heterogeneous sample. According to preferred embodiments, an agent that modifies unmethylated cytosine without modifying methylated cytosine is added to a nucleic acid sample isolated from a heterogeneous biological sample. An amplification reaction is then performed using a chimeric primer that distinguishes between a modified and an unmodified CpG dinucleotide, and specifically amplifies the unmodified CpG dinucleotide. Detection of an amplification product indicates the presence of unmodified CpG dinucleotide, which, in turn, indicates the presence of diseased cells in the sample.

According to the invention, a heterogeneous nucleic acid sample is isolated from a heterogeneous biological sample, for example, stool. A stool sample contains a highly-heterogeneous population of nucleic acids. Not only does human nucleic acid represent a small portion of the nucleic acid found in stool, but nucleic acid from cancer cells, if present, represents only a small portion of the human nucleic acid. A stool sample may contain molecular indicia of cancer, specifically, colorectal cancer, that occurs as a small subpopulation (typically on the order of about 1% at early stages of cancer or precancer) of the total human nucleic acid in the stool. Other heterogeneous biological samples may include sputum, blood, and other bodily fluids or tissues, that may or may not be mingled with other biological materials. These samples may contain nucleic acids that are indicative of a variety of diseases including cancers, e.g., prostate, breast, lung, thymus, ovarian, and so on.

According to the invention, target nucleic acid may be isolated from a heterogeneous biological sample using a sequence-specific hybrid capture step. The target template can be captured using a capture probe specific for the template. According to the invention, this hybrid capture step is preferably performed prior to CpG modification, and may result in a heterogeneous sample of target nucleic acid that contains both methylated and unmethylated forms of the target nucleic acid.

In the modification treatment, the nucleic acid sample is treated with an agent such as sodium bisulfate. Preferably, the agent modifies unmethylated cytosine to uracil without modifying methylated cytosine. Bisulfite modification treatment is described in U.S. Pat. No. 6,017,704, the entire disclosure of which is incorporated herein by reference.

After the modification treatment, an amplification reaction is preformed with at least one chimeric primer. The chimeric primer contains a first portion that is not specific for the target template and a second portion that is 3' to the first portion. In one embodiment, the second portion is specific for at least one unmodified CpG dinucleotide sequence or, preferably, for a sequence rich in CpG dinucleotides (a CpG island). In a preferred embodiment, both forward and reverse primers are chimeric primers with respective template-specific portions that hybridize with unmodified CpG sequences in the target template. The detection of an amplification product indicates methylation at the CpG sequence, preferably, hypermethylation at the CpG island. These results may indicate the onset of a particular disease, e.g., a particular cancer.

In another embodiment, the second portion of the chimeric primer is specific for at least one CpG dinucelotide sequence modified by the bisulfite treatment. Since unmethylated cytosine is modified to uracil, it will be recognized as a thymine in PCR, and the primer can be constructed accordingly to contain a template-specific portion that recognizes the modified sequences. In a heterogeneous DNA sample, such a chimeric primer can be used as a positive control for the presence of DNA in the assay, since it indicates that there is at least one copy of target DNA that is not hypermethylated. According to the invention, a primer sequence that is specific for a methylated CpG dinucleotide (a CpG dinucleotide that is not modified by treatment with a modification agent) includes a G at the position that is complementary to the C of the CpG dinucleotide. In contrast, a primer sequence that is specific for an unmethylated CpG dinucleotide (a CpG dinucleotide that is modified by treatment with a modification agent) includes an A at the position that is complementary to the C of the CpG dinucleotide, because the C is modified to a U by the modification reaction. Accordingly, a primer sequence that is specific for a plurality of CpG methylations includes a G at each position complementary to a C of each of the CpG dinucleotides in the template nucleic acid.

In an illustrative example of an assay method according to the invention, a heterogeneous DNA sample is first isolated from a biological sample (e.g., blood or stool) obtained from a patient. Three aliquots, A, B, and C, of the DNA sample are separately amplified by PCR. The PCR for aliquot A uses a conventional template-specific primer that will hybridize with a target sequence, and serves as a positive control (i.e., detection of amplicon from aliquot A indicates existence of target sequence in the sample). PCR for aliquot B uses a chimeric primer that has a 5' tail of non-specific sequence attached to the template-specific primer used in aliquot A. The melting temperature for the PCR for aliquot B may be elevated to 5° C. higher than the melting temperature used for aliquots A and C. PCR for aliquot C uses a primer that includes the non-specific sequence itself as a negative control (i.e., detection of amplicon from aliquot C indicates that the results should be disregarded due to, e.g., contamination from previous PCR). The primer used for negative control may contain bases, preferably from one to nine, in addition to the non-specific sequence, as long as the added sequence does not hybridize to any target template in the sample.

The methods of the present invention are especially suitable for applications such as; clinical assays involving sporadic cancer detection (e.g. testing DNA from stool for colorectal cancer) and related kits; and other "rare event" clinical assays and related kits. Methods of the invention may also be used for infectious disease diagnostics and related kits, and inherited disease diagnostics and related kits.

EXAMPLE 1

DNA Isolation and Sequence-specific Hybrid-capture

Stool samples were collected and prepared as described in U.S. Pat. No. 5,741,650 and in co-pending applications Ser. No. 08/876,638, filed Jun. 16, 1997, both incorporated by reference herein. Specifically, stool was collected and prepared so that a sample contained at least a cross-sectional portion of a stool voided by a patient. Alternatively, whole stool may be used. Frozen stool samples were first homogenized in a physiologically compatible buffer (e.g., having a final concentration: 500 mM Tris, 16 mM EDTA and 10 mM NaCl, pH 9.0), using an Exactor II shaker for 15 minutes. A 20% SDS solution is added to a final concentration of 0.5%. Proteinase K is also added to a final concentration of 500 µg/ml and incubated at 37° C.

Following homogenization, each sample was centrifuged twice to remove particulate matter, and the supernatant was incubated with DNAse-free RNAse. DNA was then precipitated with 300 mM sodium acetate and isopropanol, centrifuged, and resuspended in a TE buffer (10 mM Tris, 1 mM EDTA, pH 7.4).

Following preparation of total nucleic acid, DNA including a target region of interest was captured using a target-sequence specific capture probe. For example, DNA molecules carrying one of the three human gene regions described in Example 3 below were respectively captured using oligonucleotide capture probes specific for each target gene: p16, hMLH1, and MGMT. The specific capture probe for each of these target markers is listed in Table 1. Equivalent capture probes can be used for other target regions of interest. In the capture procedures, 300 µl of each sample DNA preparation was combined with an equal volume of 6M guanidinium isothiocyantate and 20 nmol of each sequence specific biotinylated oligonucleotide capture probe. The mixture was then heated to 95° C. for 5 min, cooled on ice, and incubated overnight at 25° C. Following incubation, hybridized samples were diluted with 1 ml sterile $H_2O$, 100 µl (1 mg) paramagnetic polystyrene beads coated with streptavidin (Dynabeads® M-280 Streptavidin, Dynal ASA, Oslo, Norway) was added, and the sample-bead suspension was mixed continuously and incubated for one hour at room temperature. Following incubation, the bead bound biotin-oligonucleotide-DNA complexes were then isolated with a magnetic separator and washed four times with binding and washing buffer (B&W buffer; 1 M NaCl, 10 mM Tris (pH 7.2), 1 mM EDTA, and 0.1% Tween® 20). Captured sequences were then eluted from the bead complexes by the addition of 40 µl 0.1×TE (1 mM Tris, 100 nM EDTA (pH 7.4)) and heated to 85° C. for 4 minutes.

TABLE 1

Capture probe sequences

| P16 CAPTURE PROBE | GGTGACCAGCCAGCCCCTCCTCTTTCTTCCT CCGGTG SEQ ID NO:1 |
|---|---|
| MGMT capture probe | CGAGGCTGCCACCGTCCCGAGGGAGAGCTCC GCACTC SEQ ID NO:2 |
| hMLH1 Capture probe | TCGTTTTTAGGAGCTCGGGGAATACGAAATA TCCAGCCAA SEQ ID NO:3 |

EXAMPLE 2

Sensitized Detection of Human APC Promoter Hypermethylation

Methods of the invention were used for detecting hypermethylation of CpG islands in the promoter region of human APC gene. Hypermethylation is indicative of abnormality or deficiency in APC protein's tumor suppression activity. The methods were shown to be highly sensitive in detecting small amounts of hypermethylated DNA in a heterogeneous sample.

DNA was first isolated and hybrid-captured from patients' stool samples as described in Example 1 except that the capture probe had the following sequence: CCCCG CCCAA CCGCA CAGCC TGCCT AGCCC TAGCC CC (SEQ ID NO: 4). The DNA sample then underwent bisulfite modification which converted unmethylated cytosines to uracil. Two aliquots of the bisulfite-treated samples were subjected to separate PCR. The primers used on the first aliquot were chimeric primers according to the invention, which included a 3' portion specific for a methylated target template; the primers used on the second aliquot were chimeric primers that included a 3' portion specific for an unmethylated-thus-modified target template. Amplification results from both aliquots were then subjected to gel electrophoresis, stained with ethidium bromide, and visualized.

Amplicon detected from the first aliquot is further purified and sequenced to confirm the postive result of hypermethylation. A high degree of specificity was observed for using methods of the invention in the detection assays.

Specific materials and methods for this example are as follows: DNA was modified by sodium bisulfite or other comparable agents as described in U.S. Pat. No. 5,786,146 to Herman et al., incorporated herein by reference. The bisulfite treatment modified unmethylated cytosine to uracil, which would be amplified as thymidine in the amplification product. The bisulfite treatment did not affect methylated cytosine, allowing subsequent PCR to distinguish between methylated DNA from unmethylated DNA in a heterogeneous population.

The chimeric primers used for amplifying the methylated target were 5'-GCGGT CCCAA AAGGG TCAGT TATTG CGGAG TGCGG GTC-3' for the forward primer (SEQ ID NO: 5) and 5'-GCGGT CCCAA AAGGG TCAGT TCGAC GAACT CCCGA CGA-3' for the reverse primer (SEQ ID NO: 6). The chimeric primers used for amplifying the unmethylated target, and therefore containing T (or its complement A) in place of C (or its complement G), were 5'-GCGGT CCCAA AAGGG TCAGT GTGTT TTATT GTGGA GTGTG GGTT-3' for the forward primer (SEQ ID NO: 7) and 5'-GCGGT CCCAA AAGGG TCAGT CCAAT CAACA AACTC CCAAC AA-3' for the reverse primer (SEQ ID NO: 8). All four primers have the same 5' end that is the non-specific portion: 5'-GCGGTCCCA-AAAGGGTCAGT-3' (SEQ ID NO: 9). All the oligonucleotides used in the example were HPLC purified and quantified by spectrophotometry.

PCR for each aliquot was performed in a 50 µl reaction sample with 10 µl bisulfite-treated DNA. After Hot Star polymerase (Qiagen) was added, each reaction mixture was hot-started at 95° C. for 15 minutes. The reactions were carried out in a Perkin-Ehner 9600 Thermal Cycler (Perkin-Elmer, Norwalk, Conn.) with the following temperature settings: 39 cycles of 94° C. for 30 seconds, 65° C. for 60 seconds, and 72° C. for 60 seconds. The melting/annealing temperature of 65° C. was 10° C. higher than the conventional annealing temperature used in Esterller M., et al., "Analysis of *Adenomatous Polyposis Coli* Promoter Hypermethylation in Human Cancer," 60 Cancer Research, 4366 (Aug. 15, 2000), incorporated herein by reference.

For PCR product analyses, 8 µl of the amplification reactions was loaded directly onto a 4% ethidium bromide stained agarose gel and electrophoresed at 200 V for 90 min. The amplification products were visualized with a UV transilluminator (Fotodyne, New Berlin, Wis.) and photographed with an Alpha Innotech IS-500 Digital Imaging System version 1.97 (Sun Bioscience Inc., Branford, Conn.).

Positive results of hypermethylation, i.e., the amplicon from the first aliquot, was purified using Wizard PCR Preps DNA Purification System (Promega) and sequenced out for confirmation.

EXAMPLE 3

Detection of Hypermethylation at Multiple Loci

Methods of the invention were used to screen for colorectal cancer by detecting hypermethylation of CpG islands at multiple genes or genetic loci using stool samples. Assaying for hypermethylation at multiple loci in a heterogeneous sample may provide a more reliable means of detection certain diseases.

Hypermethylation markers on three human genes p16, hMLH1, and MGMT were studied using methods of the invention. Tissue samples (colorectal mucosa) and single stools were each collected from 12 patients clinically diagnosed with colorectal cancers. Single stools were each collected from 10 colonoscopically normal controls. All stools were collected prior to cathartic cleansing for colonoscopy or surgery, and were promptly stored at –70° C.

DNA was isolated from collected tissues (colorectal mucosa) using conventional techniques (Qiagen DNA Mini Kit). DNA was isolated from collected stools and subjected to sequence-specific hybrid capture as described in Example 1 except that the hybrid-captured DNA was eluted from bead complexes directly into the alkaline solution for initiating the bisulfite modification. Bisulfite modification of DNA samples was carried out as described in Example 2. Afterwards, hypermethylated markers were assayed by PCR techniques of the invention using chimeric primers either partly specific for unmodified (hence methylated) CpG sequence, as listed in Table 2, or partly specific for modified (hence unmethylated) CpG sequence, as listed in Table 3. The DNA samples were analyzed in blinded fashion.

TABLE 2

Methylation-specific primer sequences

| Primer Designation | Sequence | Tm for PCR | SEQ ID NO. |
|---|---|---|---|
| P16 PCR forward primer | GCGGT CCCAA AAGGG TCAGT GGCGG ATCGA GTGCG TTC | 58 C | 10 |
| P16 PCR reverse primer | GCGGT CCCAA AAGGG TCAGT ACTCC CCGCC GCCCG CTA | 58 C | 11 |
| hMLH1 PCR forward primer | GCGGT CCCAA AAGGG TCAGT ATTAA TAGGA AGAGC GGATA GC | 58 C | 12 |
| hMLH1 PCR reverse primer | GCGGT CCCAA AAGGG TCAGT TTCGTC CCTCCC TAAAA CGA | 58 C | 13 |
| MGMT PCR forward primer | GCGGT CCCAA AAGGG TCAGT CGTTT TGCGT TTCGA CGTTC | 55 C | 14 |
| MGMT PCR reverse primer | GCGGT CCCAA AAGGG TCAGT CACTC TTCCG AAAAC GAAAC G | 55 C | 15 |

TABLE 3

Non-methylation-specific primer sequences

| Primer Designation | Sequence | Tm for PCR | SEQ ID NO. |
|---|---|---|---|
| P16 PCR forward primer | GCGGT CCCAA AAGGG TCAGT GGGGT GGATT GAGTG TGTTT | 58 C | 16 |
| P16 PCR reverse primer | GCGGT CCCAA AAGGG TCAGT ATACT ACTCC CCACC ACCAA | 58 C | 17 |
| HMLH1 PCR forward primer | GCGGT CCCAA AAGGG TCAGT AATGA ATTAA TAGGA AGAGT GGATA GT | 58 C | 18 |
| HMLH1 PCR reverse primer | GCGGT CCCAA AAGGG TCAGT TCTCT TCATC CCTCC CTAAA ACA | 58 C | 19 |
| MGMT PCR forward primer | GCGGT CCCAA AAGGG TCAGT TTTTT AGAAT GTTTT GTGTT TTGAT | 55 C | 20 |
| MGMT PCR reverse primer | GCGGT CCCAA AAGGG TCAGT ACCCA AACAC TCACC AAATC A | 55 C | 21 |

For tissue/mucosa samples, at least one of the three markers was found to be hypermthylated in samples from 9 out of the 12 (75%) cancer patients. Individually, the p16 marker was positive in 7 cancer patients, hMLH1 in 3 cancer patents, and MGMT in 6 cancer patients. None of the markers was found to be methylated in any tissue/mucosa samples from the 10 control patients.

For stool samples, at least one of the three markers was found to be hypermethylated in samples from 7 out of the 12 (58%) cancer patients. Out of the 9 people identified positively through the tissue samples, 7 were identified positively using methods of the invention. Individually, the p16 marker was positive in 4 cancer patients, MLH1 in 1 cancer patents, and MGMT in 4 cancer patients. The p16 marker was also positive in the stool sample of 1 control patient, and the MGMT marker in 2 of the control samples. These results may be indicia of disease in patients considered to be healthy controls. The hMLH1 marker was not positive in any of the control patients.

Therefore, the invention provides non-invasive methods for detecting indicia of cancer in heterogeneous patient samples such as stool samples.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

Incorporation By Reference

All patents, patent applications, and scientific publications mentioned herein above are incorporated by reference into this application in their entirety.

What is claimed is:

1. A method for detecting an indicia of a disease in a heterogeneous biological sample, said method comprising the steps of:
   isolating a heterogeneous nucleic-acid sample comprising a CpG-containing target template from a heterogeneous biological sample;
   contacting said nucleic-acid sample with an agent that modifies unmethylated cytosine;
   performing an amplification reaction on said target template using at least one chimeric primer that comprises a first portion that is not specific for said target template and a second portion 3' to said first portion, said second portion being specific for a methylated cytosine in said target template; and
   detecting the presence of an amplification product as an indicia of a disease.

2. A method for detecting an indicia of colorectal cancer in stool, said method comprising the steps of:
   isolating a heterogeneous nucleic-acid sample comprising a CpG-containing target template from stool;
   contacting said nucleic-acid sample with an agent that modifies unmethylated cytosine;
   performing an amplification reaction on said target template using at least one chimeric primer that comprises a first portion that is not specific for said target template and a second portion 3' to said first portion, said second portion being specific for a methylated cytosine in said target template; and
   detecting the presence of an amplification product as an indicia of colorectal cancer.

3. The method of claim 2, wherein the isolating step comprises sequence-specific hybrid capture.

4. The method of claim 2, wherein said first portion comprises at least 5, but fewer than or equal to about 30 nucleotides.

5. The method of claim 2, wherein said second portion comprises from about 10 to about 30 nucleotides.

6. The method of claim 2, wherein said first portion of each of said at least one chimeric primer is identical.

7. The method of claim 2, wherein said first portion has a G-C content of at least 50%.

8. The method of claim 2, wherein said target nucleic acid is selected from the group consisting of DNA, RNA, and a nucleic acid analog.

9. The method of claim 2, wherein said target nucleic acid is double-stranded.

10. The method of claim 2, wherein said target nucleic acid is at least a portion of a gene selected from the group consisting of human *Adenomatous Polyposis Coli* (APC) gene, p16, hMLH1, MGMT, HIC1, p14, HLTF, MINT2, and MINT31.

11. A method of screening a population of patients for colorectal cancer, the method comprising the steps of:
   isolating a plurality of target nucleic acid templates from each patient; and
   assaying each of said templates for the presence of hypermethylation according to the method of claim 2,
   wherein a patient is diagnosed as having an indicia of colorectal cancer if at least one of said templates from said patient is hypermethylated.

* * * * *

SEQUENCE LISTING

<160> NUMBER OF SEQ ID NOS: 21

<210> SEQ ID NO 1
<211> LENGTH: 37
<212> TYPE: DNA
<213> ORGANISM: Artificial Sequence
<220> FEATURE:
<223> OTHER INFORMATION: P16 capture probe

<400> SEQUENCE: 1
ggtgaccagc cagcccctcc tctttcttcc tccggtg                37

<210> SEQ ID NO 2
<211> LENGTH: 37
<212> TYPE: DNA
<213> ORGANISM: Artificial Sequence
<220> FEATURE:
<223> OTHER INFORMATION: MGMT capture probe

<400> SEQUENCE: 2
cgaggctgcc accgtcccga gggagagctc cgcactc                              37

<210> SEQ ID NO 3
<211> LENGTH: 40
<212> TYPE: DNA
<213> ORGANISM: Artificial Sequence
<220> FEATURE:
<223> OTHER INFORMATION: hMLH1 capture probe

<400> SEQUENCE: 3
tcgtttttag gagctcgggg aatacgaaat atccagccaa                           40

<210> SEQ ID NO 4
<211> LENGTH: 37
<212> TYPE: DNA
<213> ORGANISM: Artificial Sequence
<220> FEATURE:
<223> OTHER INFORMATION: EX2 capture probe

<400> SEQUENCE: 4
ccccgcccaa ccgcacagcc tgcctagccc tagcccc                              37

<210> SEQ ID NO 5
<211> LENGTH: 38
<212> TYPE: DNA
<213> ORGANISM: Artificial Sequence
<220> FEATURE:
<223> OTHER INFORMATION: chimeric primer 1

<400> SEQUENCE: 5
gcggtcccaa aagggtcagt tattgcggag tgcgggtc                             38

<210> SEQ ID NO 6
<211> LENGTH: 38
<212> TYPE: DNA
<213> ORGANISM: Artificial Sequence
<220> FEATURE:
<223> OTHER INFORMATION: chimeric primer 2

<400> SEQUENCE: 6
gcggtcccaa aagggtcagt tcgacgaact cccgacga                             38

<210> SEQ ID NO 7
<211> LENGTH: 44
<212> TYPE: DNA
<213> ORGANISM: Artificial Sequence
<220> FEATURE:
<223> OTHER INFORMATION: chimeric primer 3

<400> SEQUENCE: 7
gcggtcccaa aagggtcagt gtgttttatt gtggagtgtg ggtt                      44

<210> SEQ ID NO 8
<211> LENGTH: 42
<212> TYPE: DNA
<213> ORGANISM: Artificial Sequence
<220> FEATURE:
<223> OTHER INFORMATION: chimeric primer 4

-continued

```
<400> SEQUENCE: 8
gcggtcccaa aagggtcagt ccaatcaaca aactcccaac aa                    42

<210> SEQ ID NO 9
<211> LENGTH: 20
<212> TYPE: DNA
<213> ORGANISM: Artificial Sequence
<220> FEATURE:
<223> OTHER INFORMATION: chimeric primer 5

<400> SEQUENCE: 9
gcggtcccaa aagggtcagt                                            20

<210> SEQ ID NO 10
<211> LENGTH: 38
<212> TYPE: DNA
<213> ORGANISM: Artificial Sequence
<220> FEATURE:
<223> OTHER INFORMATION: P16 PCR forward primer

<400> SEQUENCE: 10
gcggtcccaa aagggtcagt ggcggatcga gtgcgttc                        38

<210> SEQ ID NO 11
<211> LENGTH: 38
<212> TYPE: DNA
<213> ORGANISM: Artificial Sequence
<220> FEATURE:
<223> OTHER INFORMATION: P16 PCR reverse primer

<400> SEQUENCE: 11
gcggtcccaa aagggtcagt actccccgcc gcccgcta                        38

<210> SEQ ID NO 12
<211> LENGTH: 42
<212> TYPE: DNA
<213> ORGANISM: Artificial Sequence
<220> FEATURE:
<223> OTHER INFORMATION: hMLH1 PCR forward primer

<400> SEQUENCE: 12
gcggtcccaa aagggtcagt attaatagga agagcggata gc                   42

<210> SEQ ID NO 13
<211> LENGTH: 40
<212> TYPE: DNA
<213> ORGANISM: Artificial Sequence
<220> FEATURE:
<223> OTHER INFORMATION: hMLH1 PCR reverse primer

<400> SEQUENCE: 13
gcggtcccaa aagggtcagt ttcgtccctc cctaaaacga                      40

<210> SEQ ID NO 14
<211> LENGTH: 40
<212> TYPE: DNA
<213> ORGANISM: Artificial Sequence
<220> FEATURE:
<223> OTHER INFORMATION: MGMT PCR forward primer

<400> SEQUENCE: 14
gcggtcccaa aagggtcagt cgttttgcgt ttcgacgttc                      40

<210> SEQ ID NO 15
<211> LENGTH: 41
```

```
<212> TYPE: DNA
<213> ORGANISM: Artificial Sequence
<220> FEATURE:
<223> OTHER INFORMATION: MGMT PCR reverse primer

<400> SEQUENCE: 15
gcggtcccaa aagggtcagt cactcttccg aaaacgaaac g            41

<210> SEQ ID NO 16
<211> LENGTH: 40
<212> TYPE: DNA
<213> ORGANISM: Artificial Sequence
<220> FEATURE:
<223> OTHER INFORMATION: P16 PCR forward primer

<400> SEQUENCE: 16
gcggtcccaa aagggtcagt ggggtggatt gagtgtgttt             40

<210> SEQ ID NO 17
<211> LENGTH: 40
<212> TYPE: DNA
<213> ORGANISM: Artificial Sequence
<220> FEATURE:
<223> OTHER INFORMATION: P16 PCR reverse primer

<400> SEQUENCE: 17
gcggtcccaa aagggtcagt atactactcc ccaccaccaa             40

<210> SEQ ID NO 18
<211> LENGTH: 47
<212> TYPE: DNA
<213> ORGANISM: Artificial Sequence
<220> FEATURE:
<223> OTHER INFORMATION: HMLH1 PCR forward primer

<400> SEQUENCE: 18
gcggtcccaa aagggtcagt aatgaattaa taggaagagt ggatagt     47

<210> SEQ ID NO 19
<211> LENGTH: 43
<212> TYPE: DNA
<213> ORGANISM: Artificial Sequence
<220> FEATURE:
<223> OTHER INFORMATION: HMLH1 PCR reverse primer

<400> SEQUENCE: 19
gcggtcccaa aagggtcagt tctcttcatc cctccctaaa aca         43

<210> SEQ ID NO 20
<211> LENGTH: 45
<212> TYPE: DNA
<213> ORGANISM: Artificial Sequence
<220> FEATURE:
<223> OTHER INFORMATION: MGMT PCR forward primer

<400> SEQUENCE: 20
gcggtcccaa aagggtcagt tttttagaat gttttgtgtt ttgat       45

<210> SEQ ID NO 21
<211> LENGTH: 41
<212> TYPE: DNA
<213> ORGANISM: Artificial Sequence
```

```
<220> FEATURE:
<223> OTHER INFORMATION: MGMT PCR reverse primer

<400> SEQUENCE: 21
gcggtcccaa aagggtcagt acccaaacac tcaccaaatc a                    41
```